(12) United States Patent
Yamazaki

(10) Patent No.: US 10,517,851 B2
(45) Date of Patent: Dec. 31, 2019

(54) VASOPRESSIN-LIKE ACTION ENHANCER

(71) Applicant: KYORIN PHARMACEUTICAL CO., LTD., Tokyo (JP)

(72) Inventor: Takanobu Yamazaki, Tochigi (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/775,147

(22) PCT Filed: Dec. 22, 2016

(86) PCT No.: PCT/JP2016/088283
§ 371 (c)(1),
(2) Date: May 10, 2018

(87) PCT Pub. No.: WO2017/110965
PCT Pub. Date: Jun. 29, 2017

(65) Prior Publication Data
US 2018/0344700 A1    Dec. 6, 2018

(30) Foreign Application Priority Data

Dec. 25, 2015  (JP) .................................. 2015-253018

(51) Int. Cl.
*A61K 31/4174*  (2006.01)

(52) U.S. Cl.
CPC ................................ *A61K 31/4174* (2013.01)

(58) Field of Classification Search
CPC .. A61K 31/4174; A61K 38/095; A61K 38/00; A61K 45/00
USPC ....................................................... 548/338.1
See application file for complete search history.

(56) References Cited

U.S. PATENT DOCUMENTS

2010/0255093 A1   10/2010   Edgren et al.
2011/0212984 A1    9/2011   Wun et al.

OTHER PUBLICATIONS

International Preliminary Report on Patentability dated Jun. 26, 2018 in International (PCT) Application No. PCT/JP2016/088283.

International Search Report dated Feb. 21, 2017 in International (PCT) Application No. PCT/JP2016/088283.
Shimo et al., "Relief of nocturnal enuresis by desmopressin via effect on central nervous system in a boy with primary nocturnal enuresis", Enuresis, vol. 25, 2010, pp. 19-23, Abstract and cited in ISR.
Yoshida, "Tokushu Josei Kabu Nyoro Shojo Shinryo Guideline Chiryo(2) Yakubutsu Ryoho", Voiding Disorders Digest, vol. 22, No. 2, 2014 pp. 43-49, cited in ISR.
Zaitsu et al., "Comparative evaluation of the safety and efficacy of long-term use of imidafenacin and solifenacin in patients with overactive bladder: a prospective, open, randomized, parallel-group trial" (the LIST study), Adv Urol, vol. 2011, Article ID 854697, 2011.
Han et al., "Effect of desmopressin with anticholinergics in female patients with overactive bladder", Korean J Urol, vol. 52, No. 6, 2011, pp. 396-400.
Yamazaki et al., "Imidafenacin exerts the antidiuretic effect by enhancing vasopressin-related responses in orally water-loaded rats", Eur J Pharmacol, vol. 791, Nov. 2016, pp. 72-77.
Attached document of URITOS Tablets 0.1 mg, URITOS OD Tablets 0.1 mg, revised in Jun. 2014 (11th version), 6 pages, Cited in specification.
Clinical guidelines for overactive bladder, Aug. 2005, pp. 1-5, Cited in specification.
Clinical Guidelines for nocturia, Apr. 2009, pp. 10-12, Cited in specification.
Japanese Journal of Urological Surgery, vol. 26, No. 7, 2013, pp. 1091-1098, Cited in specification.
Shimo et al., "Relief of nocturnal entiris by desmopressin via effect on central nervous system in a boy with primary nocturnal enuresis", Enuresis, vol. 15, pp. 19-23, Jun. 2010. with partial English language translation.
Extended European Search Report dated Jul. 24, 2019 in corresponding European Patent Application No. 16878852.9.

*Primary Examiner* — Kristin A Vajda
(74) *Attorney, Agent, or Firm* — Wenderoth, Lind & Ponack, L.L.P.

(57) ABSTRACT

A problem to be solved by the present invention is to provide a method for ameliorating pollakiuria and nocturia, in particular, nocturia caused by nocturnal polyuria by finding a composition that enhances the antidiuretic action of vasopressin or a vasopressin V2 receptor agonist. As a result of the studies, it has been found that imidafenacin enhances the antidiuretic action of vasopressin or the vasopressin V2 receptor agonist, whereby the present invention has been completed. According to the present invention, a composition containing imidafenacin can enhance the antidiuretic action of vasopressin or the vasopressin V2 receptor agonist, making it possible to ameliorate pollakiuria and nocturia, in particular, nocturia caused by nocturnal polyuria.

11 Claims, 3 Drawing Sheets

VASOPRESSIN-LIKE ACTION ENHANCER

TECHNICAL FIELD

The present invention relates to a composition for enhancing an antidiuretic action of vasopressin or a vasopressin V2 receptor agonist, which contains imidafenacin. Further, the present invention relates to an imidafenacin-containing antidiuretic composition, which enhances an antidiuretic action of vasopressin or a vasopressin V2 receptor agonist.

BACKGROUND ART

Imidafenacin is an anticholinergic drug that selectively inhibits muscarinic M1 and M3 receptors and currently widely used as a therapeutic drug for urinary urgency, pollakiuria, and urge urinary incontinence caused by the overactive bladder (OAB). It is believed that imidafenacin inhibits release of acetylcholine by antagonizing M1 and contraction of bladder smooth muscles by antagonizing M3 in the urinary bladder, thereby exhibiting pharmacological effects (Non-patent literature 1).

The overactive bladder, for which efficacy and effectiveness of imidafenacin are recognized, is a syndrome characterized by urinary urgency as an essential symptom and considered to be usually with pollakiuria and nocturia (Non-patent literature 2). Further, nocturia is defined as the complaint that the individual has to wake at night 1 or more times to void and it can be troublesome in itself (Non-patent literature 3).

It has been reported that imidafenacin reduces nocturnal urine volume partially by having an antidiuretic effect through the bladder sensory nerves. However, its action mechanism is not completely understood (Non-patent literature 4).

Vasopressin is known as a hormone that controls a urinary volume. Vasopressin is a peptide which is also called as an antidiuretic hormone. As a receptor of vasopressin, V1a, V1b, and V2 receptors are known. The V2 receptor is expressed in the renal collecting tubule, and binding of vasopressin to the V2 receptor promotes reabsorption of water and then reduces the urinary volume (the antidiuretic effect). Thus, a reduction in the vasopressin action causes polyuria, nocturnal enuresis, diabetes insipidus, and the like.

Further, desmopressin is known as a V2 receptor agonist that exhibits the vasopressin-like antidiuretic action. Desmopressin is also a peptide and exhibits the antidiuretic action by selectively binding to the V2 receptor. Thus, desmopressin is currently used as a therapeutic drug for nocturnal enuresis and central diabetes insipidus.

As such, a composition containing a compound that enhances the antidiuretic effect of vasopressin or the vasopressin V2 receptor agonist is considered to be useful as a composition for preventing or treating pollakiuria, nocturia, polyuria, nocturnal polyuria, nocturnal enuresis, diabetes insipidus, and the like.

CITATION LIST

Non-Patent Literature

Non-Patent Literature 1: Attached document of URITOS Tablets 0.1 mg, URITOS OD Tablets 0.1 mg, revised in June 2014 (11th version).
Non-Patent Literature 2: Clinical guidelines for overactive bladder, August 2005.
Non-Patent Literature 3: Clinical Guidelines for nocturia, April 2009.
Non-Patent Literature 4: Japanese Journal of Urological Surgery, 126 (7), 1091-1098, 2013.

SUMMARY OF INVENTION

Technical Problem

The problem to be solved by the present invention is to find a composition that enhances the antidiuretic action of vasopressin or a vasopressin V2 receptor agonist and provide a method for preventing or treating pollakiuria and nocturia, in particular, nocturia caused by nocturnal polyuria using the composition.

Solution to Problem

As a result of intensive studies, the present inventors has found that imidafenacin enhances the antidiuretic action of vasopressin or the vasopressin V2 receptor agonist, whereby the present invention has been completed. Specifically, the present invention encompasses the followings inventions.
[1] A pharmaceutical composition containing imidafenacin, wherein the pharmaceutical composition is used for enhancing an antidiuretic action of vasopressin or a vasopressin V2 receptor agonist.
[2] A composition for enhancing an antidiuretic action of vasopressin or a vasopressin V2 receptor agonist, containing imidafenacin.
[3] An antidiuretic composition containing imidafenacin, wherein the antidiuretic composition has an action of enhancing an antidiuretic action of vasopressin or a vasopressin V2 receptor agonist.
[4] An antidiuretic composition containing imidafenacin, wherein the antidiuretic composition is used with vasopressin or a vasopressin V2 receptor agonist.
[5] An antidiuretic composition containing imidafenacin, and vasopressin or a vasopressin V2 receptor agonist.
[6] The composition according to any one of [1] to [5], wherein the vasopressin V2 receptor agonist is desmopressin or a pharmaceutically acceptable salt thereof.

Advantageous Effects of Invention

According to the present invention, the antidiuretic action of vasopressin or the vasopressin V2 receptor agonist can be enhanced by imidafenacin, making it possible to prevent or treat pollakiuria and nocturia, in particular, nocturia caused by nocturnal polyuria. Further, the antidiuretic composition containing imidafenacin can be provided on the basis of the action of imidafenacin.

DESCRIPTION OF EMBODIMENTS

Figure 1:
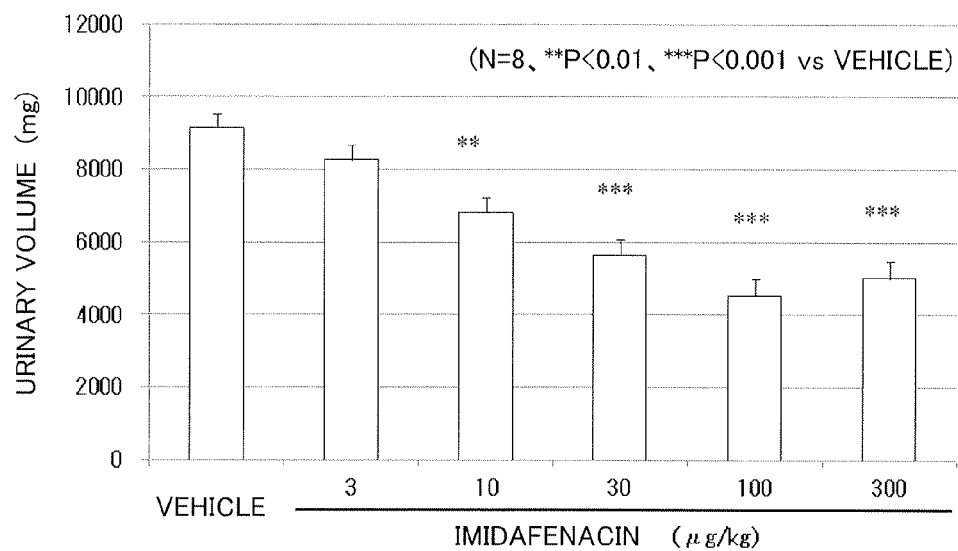
FIG. 1 is a diagram illustrating an antidiuretic action of imidafenacin.

In the present invention, imidafenacin is orally administered at a dose of preferably 0.05 to 1.0 mg per day, further preferably 0.1 to 0.4 mg per day, and particularly preferably 0.2 mg per day.

In the present invention, as an administration method of imidafenacin, the same dose as the above may be orally administered daily in two portions after breakfast and dinner or orally administered daily at one time after dinner.

In the present invention, the term "vasopressin V2 receptor agonist" refers to a compound that binds to the V2 receptor, a receptor of vasopressin, and induces a vasopressin-like action (the antidiuretic action). In the present invention, the particularly preferable vasopressin V2 receptor agonist is desmopressin or a pharmaceutically acceptable salt thereof. In the present specification, a vasopressin V2 receptor agonist and a V2 receptor agonist have the same definition.

In the present invention, the expression "enhancing the antidiuretic action of vasopressin or the vasopressin V2 receptor agonist" refers to a state in which the antidiuretic action becomes higher than that obtained by using vasopressin or the vasopressin V2 receptor agonist alone.

The composition of the present invention may include any pharmaceutically acceptable carrier. Further, the composition of the present invention may include an optional pharmaceutically acceptable additive. Examples of the additive may include an excipient, a disintegrant, a binder, a lubricant, a coating agent, a coloring agent, and a brightening agent.

Examples of the excipient may include sugars such as lactose and glucose, sugar alcohols such as D-sorbitol and mannitol, celluloses such as a crystalline cellulose, and starches such as partially pregelatinized starch and cornstarch.

Examples of the disintegrant may include celluloses such as carboxymethylcellulose calcium, a low substituted hydroxypropyl cellulose, croscarmellose sodium, and a methyl cellulose, and crospovidone.

Examples of the binder may include celluloses such as a crystalline cellulose, a hydroxypropyl cellulose, a hydroxypropyl methyl cellulose, an ethyl cellulose, and a methyl cellulose, gelatin, a polyvinyl alcohol, a partially saponified polyvinyl alcohol product, and polyvinylpyrrolidone.

Examples of the lubricant may include stearic acid and metal salts thereof, talc, hydrogenated oil, light anhydrous silicic acid, hydrated silicon dioxide, and a sucrose ester of fatty acid.

Examples of the coating agent may include celluloses such as a hydroxypropyl cellulose, a hydroxypropyl methyl cellulose, an ethyl cellulose, and a methyl cellulose, hydroxypropyl methyl cellulose phthalate, a methacrylic acid copolymer, polyvinylpyrrolidone, a stearyl alcohol, an ammonio methacrylate copolymer, an aminoalkyl methacrylate copolymer E, polyvinyl acetal diethyl aminoacetate, and a methacrylic acid copolymer (L, S).

Examples of the coloring agent may include titanium oxide, and iron sesquioxide.

Examples of the brightening agent may include carnauba wax.

The composition of the present invention may be administered, for example, in an oral dosage form, such as a tablet, a capsule, a granule, a powder, an inhalant, a syrup, a jelly, or the like, or in a parenteral dosage form, such as an injection, a suppository, a patch, or the like.

The composition of the present invention can be produced by a conventional method in the art. For example, if the composition of the present invention is in a dosage form of a film-coated tablet, it can be produced by a method described in WO2001/034147. Further, if the composition of the present invention is in a dosage form of an intraoral disintegrable tablet, it can be produced by a method described in WO2009/096559.

EXAMPLE

Example 1 Antidiuretic Action of Imidafenacin

A method according to Watanabe et al. (Watanabe et al 2013 Antidiuretic effect of antimuscanrinic agents in rat model depends on C-fibre afferent nerves in the bladder. BJU Int 112(1) 131-6) was carried out with a partial modification.

Female rats (10 to 11-week-old, obtained from Charles River Laboratories Japan) were intravenously administered (1 mL/kg) with a vehicle (saline) or imidafenacin (3, 10, 30, 100, and 300 µg/mL) and subjected to an oral water load (25 mL/kg). After the rats were transferred to Bollmann cages, urine was collected for 2 hours from each rat via a catheter previously inserted and fixed to the bladder apex of the rat (8 rats in each group).

The antidiuretic action of imidafenacin is shown in FIG. 1. As shown in FIG. 1, imidafenacin exhibited the antidiuretic action in a dose-dependent manner. Further, imidafenacin reduced the urinary volume by about 50% at the maximum.

Example 2 Antidiuretic Action of Desmopressin

The method according to Watanabe et al. (Watanabe et al 2013 Antidiuretic effect of antimuscanrinic agents in rat model depends on C-fibre afferent nerves in the bladder. BJU Int 112(1) 131-6) was carried out with a partial modification. Female rats (10 to 11-week-old, obtained from Charles River Laboratories Japan) were intravenously administered (1 mL/kg) with a vehicle (saline) or desmopressin (0.001, 0.003, 0.01, 0.03, and 0.1 µg/mL) and subjected to an oral water load (25 mL/kg). After the rats were transferred to Bollmann cages, urine was collected for 2 hours from each rat via a catheter previously inserted and fixed to the bladder apex of the rat (8 rats in each group).

Figure 2:
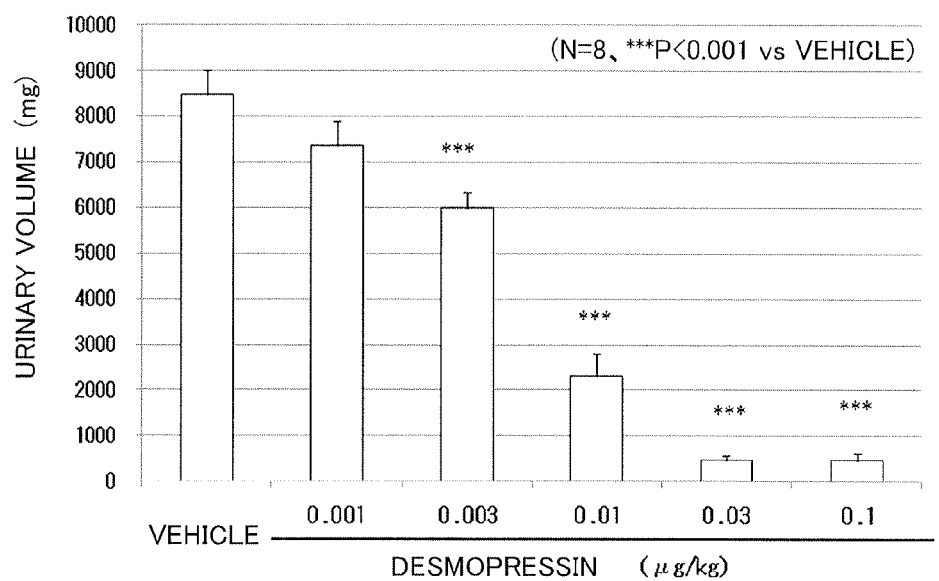
FIG. 2 is a diagram illustrating an antidiuretic action of desmopressin.

The antidiuretic action of desmopressin is shown in FIG. 2. As shown in FIG. 2, desmopressin exhibited the antidiuretic action in a dose-dependent manner. Further, desmopressin reduced the urinary volume by about 100% at the maximum.

Example 3 Combination Effect of Imidafenacin and Desmopressin

The method according to Watanabe et al. (Watanabe et al 2013 Antidiuretic effect of antimuscanrinic agents in rat model depends on C-fibre afferent nerves in the bladder. BJU Int 112(1) 131-6) was carried out with a partial modification. Female rats (10 to 11-week-old, obtained from Charles River Laboratories Japan) were intravenously administered (1 mL/kg) with a vehicle (saline), imidafenacin (10 µg/mL), desmopressin (0.003 µg/mL), or both imidafenacin and desmopressin, and subjected to an oral water load (25 mL/kg). After the rats were transferred to Bollmann cages, urine was collected for 2 hours from each rat via a catheter previously inserted and fixed to the bladder apex of the rat (8 rats in each group).

Figure 3:
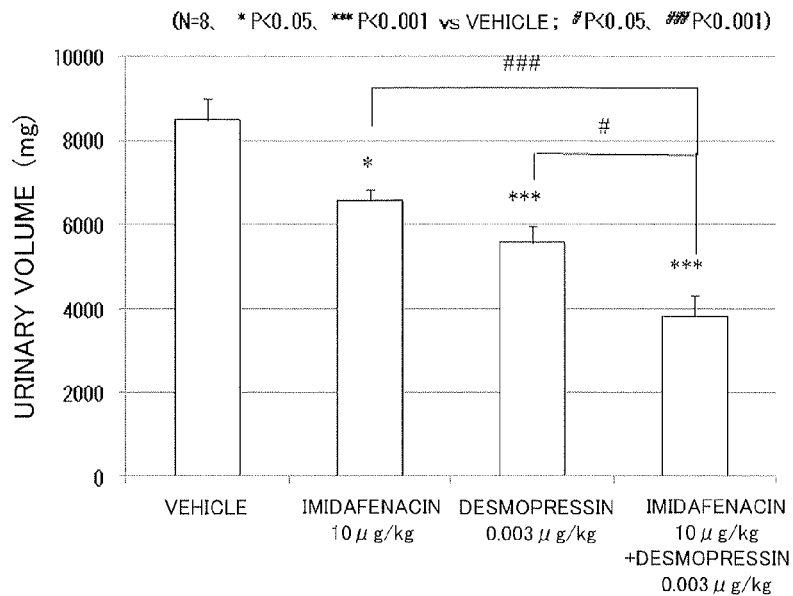
FIG. 3 is a diagram illustrating a combination effect of imidafenacin and desmopressin.

The antidiuretic action obtained by co-administration of imidafenacin and desmopressin is shown in FIG. 3. As shown in FIG. 3, the antidiuretic action was enhanced more by the co-administration of imidafenacin and desmopressin as compared to the case where imidafenacin or desmopressin was administered alone. The present invention found, for the first time, that the antidiuretic action was enhanced by the co-administration of imidafenacin and desmopressin. Further, such an enhancing effect is unexpected and surprising conclusion considering that these drugs have different action mechanisms. Further, desmopressin is an analogue of vasopressin, thus it is expected that the antidiuretic action of vasopressin is also enhanced by combination with imidafenacin as with the case of desmopressin.

Example 4 Effect of Mozavaptan on Antidiuretic Action of Imidafenacin

The method according to Watanabe et al. (Watanabe et al 2013 Antidiuretic effect of antimuscanrinic agents in rat model depends on C-fibre afferent nerves in the bladder. BJU Int 112(1) 131-6) was carried out with a partial modification. Female rats (10 to 11-week-old, obtained from Charles River Laboratories Japan) were intravenously administered with a vehicle (dimethylformamide or saline); mozavaptan (a dose of 0.1 mL/kg of a 30 mg/mL solution); 3 mg/kg of mozavaptan and imidafenacin (10 µg/kg or 300 µg/kg); 3 mg/kg of mozavaptan and desmopressin (0.003 µg/kg or 0.1 µg/kg); or 3 mg/kg of mozavaptan, imidafenacin (10 µg/kg or 300 µg/kg) and desmopressin (0.003 µg/kg or 0.1 µg/kg), and subjected to an oral water load (25 mL/kg). After the rats were transferred to Bollmann cages, urine was collected for 2 hours from each rat via a catheter previously inserted and fixed to the bladder apex of the rat (8 rats in each group).

Figure 4:
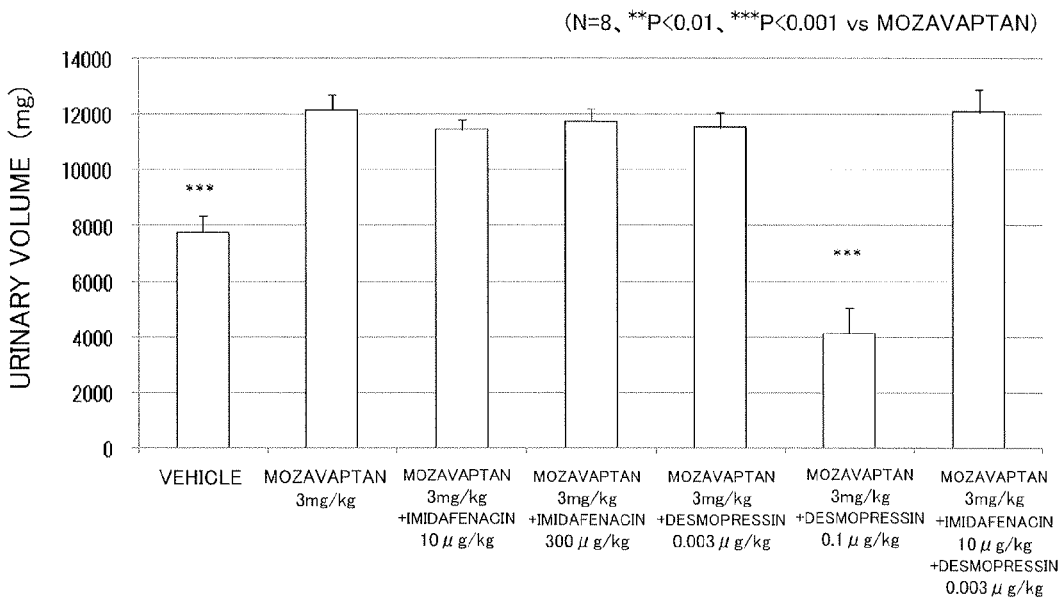
FIG. 4 is a diagram illustrating an effect of mozavaptan on the antidiuretic action of imidafenacin.
Figure 5:
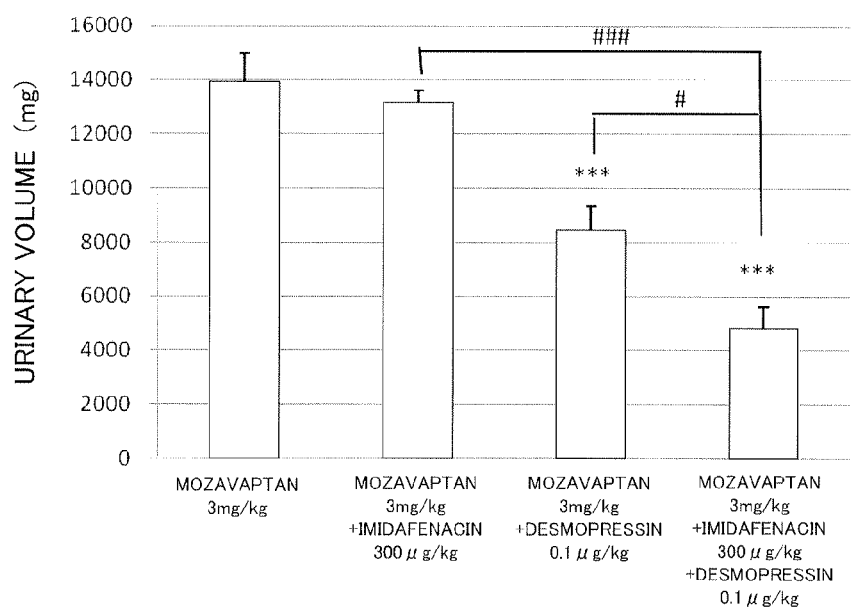
FIG. 5 is a diagram illustrating an enhancing effect of imidafenacin on the antidiuretic action of desmopressin.

Mozavaptan is a V2 antagonist that competes with vasopressin and desmopressin and inhibits their antidiuretic action. FIG. 4 shows an inhibitory action of mozavaptan on the antidiuretic action of imidafenacin or desmopressin. As shown in FIG. 4, the antidiuretic action of imidafenacin, even at the maximum reaction dose of 300 µg/kg, was completely suppressed by mozavaptan. On the other hand, although the antidiuretic action of desmopressin was also suppressed by the mozavaptan, the antidiuretic action of desmopressin was recovered by using desmopressin at the maximum reaction dose of 0.1 µg/kg. Further, as shown in FIG. 5, addition of imidafenacin at the dose of 300 µg/kg further enhanced the antidiuretic action in the group in which mozavaptan and 0.1 µg/kg desmopressin were co-administered. That is, the study showed that the administration of imidafenacin did not exhibit the antidiuretic action in a state where the antidiuretic action of endogenous vasopressin was almost completely suppressed by mozavaptan (FIG. 4), whereas the administration of imidafenacin enhanced the antidiuretic action in a state where the antidiuretic action via the vasopressin system was recovered by desmopressin (FIG. 5). These results and the result shown in FIG. 3 suggest that the vasopressin system is involved in the antidiuretic action of imidafenacin and imidafenacin exhibits its antidiuretic action by enhancing the vasopressin activity. The present invention found, for the first time, that the vasopressin system was involved in the antidiuretic action of imidafenacin. Further, the previous report (Watanabe et al 2013 Antidiuretic effect of antimuscanrinic agents in rat model depends on C-fibre afferent nerves in the bladder. BJU Int 112(1) 131-6) showed that release of vasopressin was not affected by imidafenacin in rat, leading to the conclusion that vasopressin was not involved in the antidiuretic action of imidafenacin. Thus, the present invention has unexpected advantageous effects with surprising results.

INDUSTRIAL APPLICABILITY

According to the present invention, it is expected that pollakiuria and nocturia, in particular, nocturia caused by nocturnal polyuria can be prevented or treated by enhancing the antidiuretic action of vasopressin or the vasopressin V2 receptor agonist using imidafenacin.

The invention claimed is:

1. A pharmaceutical composition comprising imidafenacin and vasopressin or a vasopressin V2 receptor agonist.

2. The pharmaceutical composition according to claim 1, wherein the vasopressin V2 receptor agonist is desmopressin or a pharmaceutically acceptable salt thereof.

3. The pharmaceutical composition according to claim 1, further comprising a pharmaceutically acceptable carrier.

4. A method of enhancing the antidiuretic action of vasopressin or a vasopressin V2 receptor agonist, comprising administering a therapeutically effective amount of imidafenacin to a patient in need thereof.

5. The method according to claim 4, wherein the imidafenacin is administered in the form of a pharmaceutical composition comprising the imidafenacin and a pharmaceutically acceptable carrier.

6. The method according to claim 4, further comprising administering a therapeutically effective amount of vasopressin or a vasopressin V2 receptor agonist to the patient.

7. The method according to claim 6, wherein the vasopressin V2 receptor agonist is desmopressin or a pharmaceutically acceptable salt thereof.

8. The method according to claim 4, wherein the imidafenacin is administered at a dose of 0.05 to 1.0 mg per day.

9. The method according to claim 4, wherein the imidafenacin is administered at a dose of 0.1 to 0.4 mg per day.

10. The method according to claim 4, wherein the imidafenacin is administered twice per day.

11. The method according to claim 4, wherein the imidafenacin is administered orally.

* * * * *